United States Patent
Smith et al.

(10) Patent No.: US 7,309,809 B2
(45) Date of Patent: Dec. 18, 2007

(54) ADHESIVE ATTACHMENT AND REMOVAL DEVICE

(75) Inventors: David Smith, Richmond, IN (US); Owen L. Johns, Madeira Beach, FL (US)

(73) Assignee: Xennovate Medical LLC, Richmond, IN (US)

( * ) Notice: Subject to any disclaimer, the term of this patent is extended or adjusted under 35 U.S.C. 154(b) by 0 days.

(21) Appl. No.: 11/343,661

(22) Filed: Jan. 31, 2006

(65) Prior Publication Data

US 2006/0195054 A1   Aug. 31, 2006

Related U.S. Application Data

(60) Provisional application No. 60/656,607, filed on Feb. 26, 2005.

(51) Int. Cl.
*A61F 13/00* (2006.01)
*A61F 15/00* (2006.01)

(52) U.S. Cl. .............. 602/57; 602/41; 602/54; 602/55

(58) Field of Classification Search ........ 602/54, 602/56, 57, 41–43, 47, 52, 55, 2
See application file for complete search history.

(56) References Cited

U.S. PATENT DOCUMENTS

| | | | |
|---|---|---|---|
| 3,339,546 A | 9/1967 | Chen | |
| 3,880,159 A * | 4/1975 | Diamond | 602/58 |
| 3,991,754 A | 11/1976 | Gertzman | |
| 4,051,848 A | 10/1977 | Levine | |
| 4,133,310 A | 1/1979 | Lloyd et al. | |
| 4,187,851 A | 2/1980 | Hauser | |
| 4,243,656 A | 1/1981 | Walliczek | |
| 4,540,409 A | 9/1985 | Nystrom et al. | |
| 4,572,814 A | 2/1986 | Naylor et al. | |
| 4,581,026 A | 4/1986 | Schneider | |
| 4,588,580 A | 5/1986 | Gale et al. | |
| 4,597,961 A | 7/1986 | Etscorn | |
| 4,727,868 A | 3/1988 | Szycher et al. | |
| 4,753,231 A | 6/1988 | Lang et al. | |
| 4,769,020 A | 9/1988 | Eaton | |
| 4,860,737 A | 8/1989 | Lang et al. | |
| 4,884,563 A * | 12/1989 | Sessions | 602/57 |
| 4,915,950 A | 4/1990 | Miranda et al. | |
| 4,921,704 A | 5/1990 | Fabo | |
| 4,995,392 A | 2/1991 | Lang et al. | |
| 5,100,672 A | 3/1992 | Gueret et al. | |
| 5,147,338 A | 9/1992 | Lang et al. | |

(Continued)

FOREIGN PATENT DOCUMENTS

JP   10 328268   12/1998

(Continued)

*Primary Examiner*—Justine R. Yu
*Assistant Examiner*—Kristen Matter
(74) *Attorney, Agent, or Firm*—Maginot, Moore & Beck

(57) ABSTRACT

An adhesive dressing comprises a substrate formed by an apertured removal layer embedded within an adhesive layer, wherein the removal layer facilitates easy and a traumatic removal of the dressing from a patient's skin. The removal layer may takes the form of an open net-like material that may extend beyond one or more edges of the adhesive layer for grasping with the fingers, attaching auxiliary devices, or other purposes.

25 Claims, 1 Drawing Sheet

U.S. PATENT DOCUMENTS

| | | | |
|---|---|---|---|
| 5,154,706 A * | 10/1992 | Cartmell et al. | 604/307 |
| 5,340,363 A * | 8/1994 | Fabo | 604/304 |
| 5,423,784 A | 6/1995 | Metz | |
| 5,445,604 A | 8/1995 | Lang | |
| 5,520,629 A * | 5/1996 | Heinecke et al. | 602/57 |
| 5,531,725 A | 7/1996 | Steer | |
| 5,593,389 A | 1/1997 | Chang | |
| 5,632,731 A * | 5/1997 | Patel | 602/59 |
| 5,662,928 A | 9/1997 | Braun | |
| 5,681,579 A | 10/1997 | Freeman | |
| 5,709,651 A * | 1/1998 | Ward | 602/57 |
| 5,840,052 A * | 11/1998 | Johns | 602/54 |
| 5,861,348 A * | 1/1999 | Kase | 442/184 |
| 5,891,077 A * | 4/1999 | Gilman et al. | 602/57 |
| 6,225,521 B1 | 5/2001 | Gueret | |
| 6,321,421 B1 | 11/2001 | Lim | |
| 6,479,724 B1 | 11/2002 | Areskoug et al. | |
| 6,635,037 B1 | 10/2003 | Bennett | |
| 2004/0049146 A1* | 3/2004 | Kolte et al. | 602/61 |
| 2005/0013957 A1* | 1/2005 | Leschinsky | 428/40.1 |
| 2005/0043658 A1* | 2/2005 | Rix | 602/2 |
| 2006/0003133 A1* | 1/2006 | Johnson | 428/40.1 |
| 2006/0142687 A1* | 6/2006 | Liedtke et al. | 602/58 |
| 2006/0161088 A1* | 7/2006 | Voetsch | 602/43 |

FOREIGN PATENT DOCUMENTS

| JP | 2002 045232 | 2/2002 |
|---|---|---|

\* cited by examiner

ADHESIVE ATTACHMENT AND REMOVAL DEVICE

REFERENCE TO RELATED APPLICATION

This application claims priority to co-pending provisional application No. 60/656,607, filed on Feb. 26, 2005, the disclosure of which is incorporated herein by reference.

BACKGROUND OF THE INVENTION

The present invention concerns adhesive dressings and in particular dressings having an adhesive surface for adhering to the skin of a patient.

Adhesive dressings and devices are well known in the art for use as wound coverings, device fixation and other health applications. Specific applications of such adhesive dressings may be found in the area of wound dressings, drug delivery, finger bandages, urinary catheters and ostomy sealing materials. It is generally known to combine adhesives with an occlusive film, cloth or foam outer backing layer to protect and aid in the removal of the adhesive device. For instance, U.S. Pat. No. 3,339,546 discloses a bandage which comprises a waterproof film of a material such as polyethylene, and a water absorbent hydrocolloid adhesive, with the adhesive mass firmly attached to the backing. Numerous other patents disclose various compositions for absorbent adhesives containing mixtures of a sticky elastomer, such as polyisobutylene, and mixtures of hydrocolloid gums, such as pectin, carboxymethylcellulose, karaya and other tackifiers and plasticizers. See, e.g., U.S. Pat. Nos. 4,813,942 and 6,326,421.

In general, prior devices utilize an occlusive film, foam or laminations of similar materials that form an attached outer backing to protect the adhesive and serve as an upper support means for strengthening the weak adhesive mass, as well as to facilitate removal after use. Certain formulations are known for fluid absorptive adhesives that will attach a collector housing to a body surface for covering wounds. Removal of these devices is accomplished by pulling a flexible film backing attached to the adhesive layer.

Although widely used, human skin adhesives have relatively low cohesive strength. Since absorptive adhesives are filled with water absorbent particles, they lose even more cohesive strength in use as the particles swell while absorbing moisture from the skin and other body fluids. Cohesive failure of the adhesive in a wound covering may become a significant problem requiring constant attention in case the dressing becomes compromised. This problem is further exacerbated when absorptive adhesive dressings leave residue or gel-like material behind on sensitive skin areas or in a wound.

No prior adhesive devices have adequately addressed the removal problems associated with such adhesives. Removal of the prior devices requires that the edge of the adhesive layer or dressing be lifted, usually by scratching with a fingernail, to pull off the combined backing layers and adhesive mass. This frequently results in adhesive left on the patient's skin, on the fingers or gloves of the medical personnel, and/or within the wound bed. Cleaning this residue with solvents is often required, which may lead to further irritation or injury.

SUMMARY OF THE INVENTION

The present invention eliminates these shortcomings and simultaneously provides opportunities for attachment of auxiliary devices, medication delivery and other unique applications, such as delivering or detecting electrical fields. The present invention thus provides an improved adhesive construction suitable for medical use as a wound dressing, first aid dressing, or in connection with attachment devices such as ostomy bags, external urinary catheters, monitoring electrodes, intravenous catheter fixation, iontophoretic dressings and other similar applications. The unique removal means incorporated into this adhesive construction increases patient comfort and provides complete removal of the adhesive layer of the device, substantially free of any residue left on the patient's skin. Moreover, the removal means of this invention can be manipulated by any person, whether medical or non-medical personnel.

More specifically, the present invention relates to an adhesive device that includes a net-like material in the adhesive contact face. With the netting on or adjacent the contact surface of the dressing, the force required to remove the adhesive device from the adherend (i.e., the patient's skin) is reduced since it is acting at the bottom of the adhesive mass, rather than at the top. In accordance with the preferred embodiment of the invention, the adhesive has a greater affinity for the net-like material than for human skin, so that the adhesive layer preferentially comes off with the netting, leaving no adhesive residue. Moreover, the proximity of the removal layer or netting to the adherent surface reduces the likelihood of the patient's hair becoming embedded within the adhesive layer, further facilitating removal of the adhesive device.

The present invention further provides for lower removal forces at the adhesive/adherend interface than prior wound dressings. This lower removal force means less discomfort to the patient and may allow higher initial adhesion levels to be used without distressing the skin upon removal. Indeed, this ease of removal may allow adhesive devices to be used in highly sensitive skin areas, such as around the male and female genital regions that ordinarily do not tolerate prior adhesive devices due to their inherent difficulty of removal and the presence of adhesive residue upon removal.

The net-like or apertured material of the present invention is disposed on or adjacent the adhesive face, partially embedded or generally flush with the contact surface level of the adhesive mass. One benefit associated with the positioning of the net-like material is that the adhesive mass adheres to the net-like material surrounding each aperture opening in the material. Thus, if a netting material is selected that has an affinity to the adhesive that is greater than the affinity of the adhesive to the skin, then the adhesive will be pulled away at a multiplicity of small areas, facilitating complete removal.

In general, an adhesive or absorptive adhesive composition or laminate according to the present invention comprises a layer of predominantly open area net-like material attached to or adjacent the adhesive face used for adhesion to a surface. The net-like material may approximate the external bounds of the adhesive but preferably extend beyond the adhesive layer on one or more sides.

According to one embodiment of the invention, a laminate which may be used as an adhesive dressing, comprises a temporary or permanent protective backing on a first surface of an adhesive layer with a layer of material containing openings or apertures therein impressed on or adjacent an opposite second surface of the adhesive layer to facilitate removal after use. The adhesive layer may be a pressure sensitive adhesive suitable for use on human skin. The layer of apertured material operates as a removal layer; with the adhesive layer being substantially indwelling within the plurality of apertures or openings. In one preferred embodiment, the removal layer includes 5-100 openings per square centimeter. In another feature, the laminate may included a release layer disposed over and protecting the second surface of the adhesive layer until it is desired to attach the laminate to an adherend.

In certain embodiments, the indwelling material of the removal layer may extend beyond the periphery of the adhesive portion of the dressing in one or more locations. This extended material forms a flap that may be easily grasped and pulled to remove the laminated dressing from the patient's skin, for instance. One benefit of this extended flap or tab is that it can be easily grasped by the gloved hand of medical personnel, or by a person with limited manual dexterity. It can further be appreciated that this flap of the removal layer is devoid of adhesive so the person removing the laminate will not come into contact with any adhesive material.

Other features of the inventive adhesive laminate include forming the adhesive layer of an absorbent material and forming the removal layer of a warp knit netting, non-woven scrim, extrusion formed netting, open cell foam or other similar porous material. The removal layer may also be electrically conductive and/or coated with or containing drugs, bactericides, herbal compounds or other therapeutic agents.

In another aspect of the invention, an adhesive dressing comprises a temporary or permanent protective backing on a first surface of an adhesive layer, with a removal layer of material containing apertures on or adjacent the opposite second surface to facilitate removal after use. In this embodiment, secondary devices may be attached to the removal layer for conduction, capillary infusion, capillary drainage and transport of chemicals or energy to the dressing face. The adhesive dressing may further comprise an extension of the net-like material that forms a flap or removal tab projecting beyond the body of the dressing.

It is therefore one object of the present invention to provide a laminated adhesive product with a unique removal means for application to human skin or other surfaces. Another object resides in the laminated absorptive adhesive product having a net-like layer on at least one adherend-contacting face to facilitate application, removal, attachment of devices, electrical conductance, liquid removal and/or delivery of medications.

An additional object of the invention is to facilitate removal and reduce residue of swollen absorptive adhesive dressings from sensitive skin areas and wounds. These and other objects of the present invention, together with several advantages thereof, will become apparent upon consideration of the following written description and accompanying figures.

DESCRIPTION OF THE PREFERRED EMBODIMENTS

Figure 1:
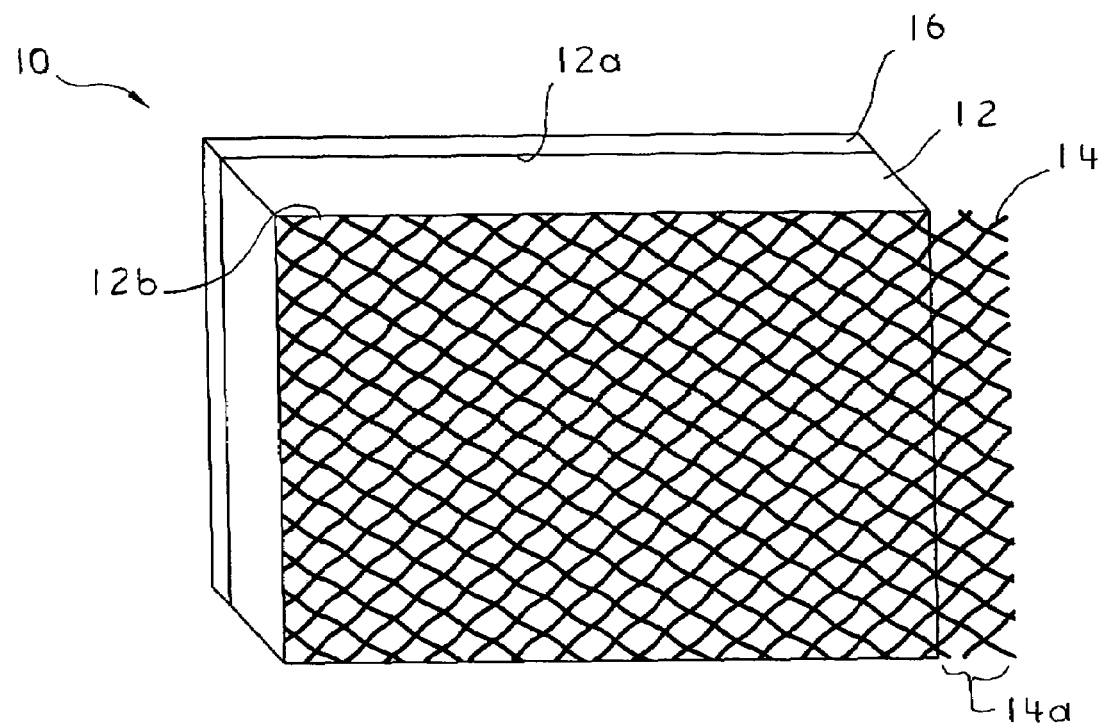
FIG. 1 is a perspective view of a laminate according to one embodiment of the present invention in which the removal layer is at a surface of the adhesive layer.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
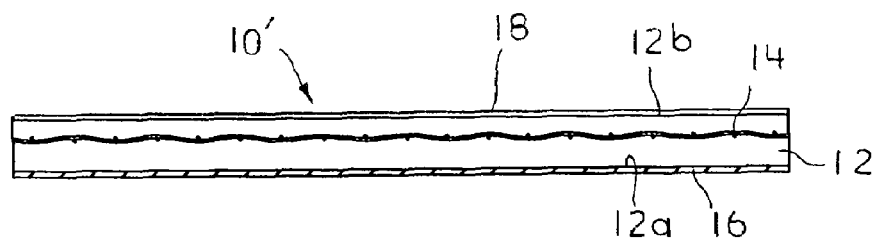
FIG. 2 is a cross-section view of a laminate according to a further embodiment of the invention in which the removal layer is embedded within the adhesive layer adjacent the surface.

In one embodiment of the invention, a laminate 10 comprises an absorptive adhesive layer 12 and a removal layer 14, as illustrated in FIG. 1. In some constructions, a backing layer 16 made of film, foam or combined layers of such flexible materials may be present on the surface 12a of the adhesive layer. In addition, a removable release liner 18 may cover the surface 12b of the adhesive layer opposite the backing layer 16, as depicted in FIG. 2. For other uses, both surfaces 12a, 12b may be covered with a removable release liner like liner 18, with the liner on surface 12b removed prior to application of the laminate to a patient's skin and the liner on surface 12a removed for attachment of an accessory. All layers other than the adhesive layer may be extended beyond the outer periphery of the adhesive layer on one or more perimeter bounds. In the preferred embodiment, the removal layer 14 extends beyond at least one end or side of the adhesive layer 12 a sufficient distance to provide a flap 14a that can be manually grasped for removal of the laminate 10 from the patient's skin.

The removal layer 14 includes a plurality of openings in which the combined area of the openings is greater than five percent (5%) of the total surface area of the layer. Most preferably, the combined area of the openings is a significantly greater percentage of the total area of the layer, in the range of 50-60%. In a preferred embodiment, the layer 14 is a composition of a net-like material comprised of nylon, rayon, high and low density polyethylene, polypropylene, EVA, cellulose, cotton, metallic or any other flexible fiber intertwined into a woven or entangled structure. The removal layer is sufficiently open or porous to allow the adhesive material forming the adhesive layer 12 to pass through the openings and make contact with the adherend or application site.

Most preferably, the removal layer 14 resides at the surface 12b of the adhesive layer to contact the skin, as shown in FIG. 1, or immediately adjacent to the surface 12b, as in the laminate 10' shown in FIG. 2. The removal layer 14 may be more or less extensible or stretchable in one or both directions as suits the particular application of the laminate 10. In some applications, such as an adhesive dressing for elbows or knees, it may be desirable to have the removal layer be easily deformable or extensible to conform to the contour of the desired dressing location and still provide solid adhesive contact with the skin area.

The removal layer material may also be coated or impregnated with therapeutic substances. For instance, the removal layer 14 may be pre-coated with therapeutic drugs, bactericides, herbal compounds, and even electrical ions. The removal layer material may exhibit conductivity to provide adjunct functionality to the laminate 10/10'. For instance, the removal layer 14 may exhibit electrically conductive properties for use in pH detection at the adherend, which may facilitate detection of sepsis conditions at a wound site. The removal layer may also be thermally conductive, either to aid in sensing heat or dispersing heat to or from the adherend. The layer 14 may also exhibit fluid conductive properties to aid in the transport of chemicals to the adherend. For instance, the layer may permit capillary transport of materials from outside the laminate to the surface 12b in contact with the skin or wound. The flap 14a of the removal layer may be used to attach secondary devices that are operable to utilize the conductive features of the layer noted above.

A preferred material for the removal layer 14 is tulle, a warp knitted netting made from several filaments of about 40 dernier nylon. One specific tulle material is sold by Hirschberg and Schlutz & Co., Inc., of Union, N.J. Warp-knit tulle does not rip easily, does not unravel, and has multiple yarn material choices, such as cotton, silk, nylon and polymeric spin filaments. Other suitable materials for the removal layer 14 are manufactured by InterNet, Inc. of Minneapolis, Minn. and by DelStar Technologies, Inc. of Middletown, Del., including a line of extruded and formed netting materials sold under the product names of NAL-TEX®, DELNET®, and STRATEX®.

Adhesives particularly well suited to form the adhesive layer 12 for use with the removal layer 14 are pressure sensitive adhesives, meaning that they can adhere to a surface, such as human skin, upon application of pressure. A particularly suitable class of pressure sensitive adhesives includes absorbent adhesives commonly known as hydrocolloids. Many formulations of hydrocolloids exist and are generally comprised of polyisobutylene rubber, one or more water soluble hydrocolloid gums, particulate reinforcements and mineral oil. Other chemicals, such as various antioxidants, may be added for stability. One known acceptable hydrocolloid adhesive is disclosed in U.S. Pat. No. 4,551,490, the disclosure of which is incorporated herein by reference. The polyisobutylene rubber employed in the adhesive disclosed in the '490 patent has a low molecular weight, on the order of from about 36,000 to about 60,000 (Florey). Such polyisobutylenes are commercially available under the product name OPPANOL® from BASF Corporation as grades B15SFN and B150.

The adhesive layer 12 is preferably formed of a liquid absorbent material that can absorb body fluids at the adherend site. Thus, the adhesive layer may absorb sweat, blood, wound seepage or other bodily fluids at the site. As indicated above, in certain embodiments the removal layer 14 may also be liquid absorbent to assist in wicking fluids away from the attachment site.

Acrylic adhesives and many other pressure sensitive adhesive systems may also be used, such as acrylic adhesives manufactured by Rohm & Haas Co., Monsanto and National Starch Company. Silicone pressure sensitive adhesives, such as those produced by Dow Corning Corp., may also be used to form the layer 12 of the present invention. The chemical families of pressure sensitive adhesives are not limited to the adhesive mentioned above, but may include other adhesives or combinations thereof that are suitable for adhering to a patient's skin. In accordance with one feature of certain embodiments of the invention, suitable adhesives will have a greater affinity for the material of the removal layer 14 than for the patient's skin.

In one example, a 20 mil thick adhesive layer 12 includes a 1 mil thick backing layer 16. A tulle mesh removal layer 14 is disposed within the adhesive layer to that no portion of the removal layer lies outside or is exposed at the surface 12b. The tulle mesh in this example has 32 openings per square inch. In other examples, the tulle mesh may have 5-100 openings per square centimeter.

In another example, the tulle mesh has 32 openings per sq. in. and the openings are configured so that the mesh exhibits only minimal elongation when pulled at one end. This mesh is merged into active surface of the adhesive layer. In comparison to a standard adhesive layer, the laminate of this embodiment demonstrated a 33% lower removal force. The measured amount of residual adhesive remaining on the patient's skin was less than two percent.

According to one embodiment of the invention, the laminate may be produced by unwinding the removal layer 14, such as the tulle netting, along a face of a release liner 18. A mass of adhesive, such as the hydrocolloid adhesives described above, is rolled onto the removal layer 14 so that the adhesive mass is impressed into the release layer. The backing layer 16 may be added to the exposed surface 12b of the adhesive mass to define the adhesive layer 12. The entire laminate may be slightly compressed until the adhesive layer is sufficiently cured to hold the laminate construction together. In this method, the resulting laminate will appear as in FIG. 1, with the removal layer 14 positioned at the surface 12b of the adhesive layer 12. It is understood that in accordance with this method, a single adhesive dressing may be formed by combining appropriately sized release liner, removal layer and backing layer. Alternatively, this method may be used to form a continuous strip or sheet of laminate from which individual adhesive dressings may be cut. In one preferred embodiment, the method is used to form a continuous strip of laminate in which the removal layer 14 is sized to form the flap 14a at one edge of the laminate.

According to another embodiment, the laminate may be formed by temporarily removing the release liner 18 from a previously fabricated dressing of adherent device. The removal layer 14 is then laminated into the adhesive layer 12 of the dressing, which may require heating the dressing to allow the adhesive to receive the layer 14. In this approach, the removal layer may be at the surface of the adhesive layer, as shown in FIG. 1, or may be manipulated to be embedded within the adhesive adjacent eh exposed surface 12b. The release liner may then be replaced.

Other methods for fabricating the laminate 10/10' are contemplated, such as coating one or both sides of an apertured removal layer, dipping and scraping one face of the netting or spraying adhesive into the netting. In any of these alternative approaches, the position of the removal layer 14 may be at or adjacent the surface 12b of the adhesive layer 12.

The present invention contemplates incorporation of a removal layer into the underside of an adhesive device, which affords easier handling, firm attachment, lower removal force and substantially complete containment of adhesive mass upon removal. While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:
1. A laminate for attachment to a patient's skin, comprising:
an adhesive layer of an adhesive adapted for removable attachment at one surface thereof to the patient's skin; and a removal layer embedded within said adhesive layer at or flush with said one surface, said removal layer defining a plurality of openings with said adhesive passing therethrough, wherein said adhesive has a greater adherent affinity for said removal layer than for the patient's skin.

2. The laminate of claim 1, wherein said adhesive is a pressure sensitive adhesive material.

3. The laminate of claim 1, wherein said removal layer includes between 5 and 100 openings per square centimeter.

4. The laminate of claim 1, wherein said removal layer is sized so that a portion of said removal layer projects beyond a portion of the periphery of said adhesive layer sufficient to be grasped for removal of the laminate from the patient's skin.

5. The laminate of claim 1, further comprising a backing layer on a surface of said adhesive layer opposite said one surface.

6. The laminate of claim 1, further comprising a release liner removably covering said one surface of said adhesive layer.

7. The laminate of claim 1, wherein said openings of said removal layer constitute at least five percent (5%) of the total surface area of the removal layer.

8. The laminate of claim 1, wherein said removal layer is formed from a material selected from the group of a warp-knit netting, a non-woven scrim, an extrusion formed netting, and an open-cell foam.

9. The laminate of claim 1, wherein said removal layer is formed from a material that is electrically or thermally conductive for conduction from an external source.

10. The laminate of claim 1, wherein said removal layer is formed of an absorbent material.

11. The laminate of claim 1, wherein said adhesive layer is formed of a water absorbent material.

12. A laminate for attachment to a patient's skin, comprising:

an adhesive layer of an adhesive adapted for removable attachment at one surface thereof to the patient's skin; and a removal layer embedded within said adhesive layer at or flush with said one surface, said removal layer defining a plurality of openings with said adhesive passing therethrough, wherein said removal layer is sized so that a portion of said removal layer projects beyond a portion of the periphery of said adhesive layer.

13. The laminate of claim 12, wherein said adhesive is a pressure sensitive adhesive material.

14. The laminate of claim 12, wherein said removal layer includes between 5 and 100 openings per square centimeter.

15. The laminate of claim 12, further comprising a backing layer on a surface of said adhesive layer opposite said one surface.

16. The laminate of claim 12, further comprising a release liner removably covering said one surface of said adhesive layer.

17. The laminate of claim 12, wherein said openings of said removal layer constitute at least five percent (5%) of the total surface area of the removal layer.

18. The laminate of claim 12, wherein said removal layer is formed from a material selected from the group of a warp-knit netting, a non-woven scrim, an extrusion formed netting, and an open-cell foam.

19. The laminate of claim 12, wherein said removal layer is formed from a material that is electrically or thermally conductive for conduction from an external source.

20. The laminate of claim 12, wherein said removal layer is formed of an absorbent material.

21. The laminate of claim 12, wherein said adhesive layer is formed of a water absorbent material.

22. A method for forming an adhesive laminate comprising the steps of:

providing a release liner;

overlaying the release liner with a removal layer having a plurality of openings therethrough; and impressing an adhesive onto the removal layer so that adhesive becomes embedded within the plurality of openings and so that the adhesive contacts the release liner, to thereby form an adhesive layer with the removal layer embedded within said adhesive at or flush with a surface of said adhesive adapted for removable attachment to a patient's skin.

23. The method of claim 22, further comprising applying a backing layer to the exposed surface of the adhesive layer.

24. The method of claim 22, wherein the step of impressing the adhesive includes embedding the removal layer so that the removal layer is at the surface of the adhesive layer in contact with the release liner.

25. The method of claim 22, wherein the step of impressing the adhesive includes embedding the removal layer so that the removal layer is adjacent the surface of the adhesive layer in contact with the release liner.

* * * * *